US00PP09639P

United States Patent [19]

Bergman

[11] Patent Number: Plant 9,639

[45] Date of Patent: Sep. 3, 1996

[54] *JUNIPERUS HORIZONALIS* CV. MONBER

[75] Inventor: Willis A. Bergman, Quincy, Ill.

[73] Assignee: Monrovia Nursery Company, Azusa, Calif.

[21] Appl. No.: 497,067

[22] Filed: Jun. 30, 1995

[51] Int. Cl.[6] ..... A01H 5/00

[52] U.S. Cl. ..... Plt./50.2

[58] Field of Search ..... Plt./50.2

[56] References Cited

U.S. PATENT DOCUMENTS

P.P. 2,752 7/1967 Lee ..... Plt./50.2

P.P. 2,773 10/1967 Lee ..... Plt./50.2

*Primary Examiner*—James R. Feyrer

[57] ABSTRACT

A new and distinct selection of Ground Juniper shrub which shall be referred to hereinafter as *Juniperus horizontalis* cultivar Monber. *Juniperus horizontalis* cultivar Monber differs distinctively from other *Juniperus horizontalis* plants by its unique combination of a brilliant silvery blue color and the ability to retain a dense crown that does not open and become bare with age.

1 Drawing Sheet

BACKGROUND OF THE NEW PLANT

This invention relates to a new and distinct selection of *Juniperus horizontalis* a member of the Cupressaceae or cypress family. *Juniperus horizontalis* cultivar Monber was discovered as a sport of *Juniperus horizontalis* 'Wiltonii' around the year 1978. This sport was propagated as it exhibited a brilliant silvery blue color and later was observed to retain a dense crown. My new plant has been asexually reproduced by cuttings since the discovery at Bergman Nursery, 3607 North 12th, Quincy, Ill., 62301 and later at two locations of Monrovia Nursery Company, 13455 S.E. Lafayette Hwy, Dayton, Ore. and 18331 E. Foothill Blvd. Azusa, Calif. This plant substantially differs from its parent variety 'Wiltonii' in its foliage coloration, its higher level of non-juvenile needles, its presentation and retention of foliage and branches in the crown portion of the plant, and in its comparatively overall enhanced, more robust appearance. These characteristics set the claimed plant apart from the parent 'Wiltonii' and other varieties of *J. horizontalis* of which I am aware. Had the initial sport not been discovered and separated by me,, it might have been lost to mankind. Because this plant has not been observed to form berries, it is not apparent that the desired characteristics of this plant could be conveyed to progeny through sexual reproduction. However, the extensive testing of this plant through both the rooting of cuttings and grafting, as disclosed above, has established that the novel, exceptional characteristics of this plant are stable and reliably passed on to clonal specimens through asexual reproduction.

SUMMARY OF THE INVENTION

*Juniperus horizontalis* cv. Monber is unusual for the winter color it displays. The silvery blue color becomes more distinct and with early or late frost a luminous glow is visible. Neither the cultivars 'Waukegan' nor 'Wiltonii' exhibit this silvery blue foliage color.

Juvenile foliage which is needle-like in shape is practically nonexistent on my new selection composing of approximately 1 percent of the total foliage. The 'Wiltonii' selection does exhibit a slightly higher amount of juvenile foliage of approximately 5 percent of the total foliage.

Other than color the most obvious difference is growth habit of my new selection. My selection maintains a dense well foliated central crown made up of branchlets which are shorter and thicker producing a dense well covered plant. In comparison, 'Wiltonii' possesses longer and narrower (rope-like) branchlets which do not cover densely and therefore exhibits the bare central horizontal branching.

BRIEF DESCRIPTION OF DRAWINGS

The upper photograph is a foliage close up of cultivar Monber exhibiting a silvery blue color to the foliage.

The lower photograph displays the growth habit of my selection. The short branchlets provide a thick well covered prostrate shrub with no center dieback or bare branches.

BOTANICAL DESCRIPTION

Below is a detailed description of my new selection of *Juniperus horizontalis* cv Monber, the color terminology is from the British Horticultural Color Charts.

Overall size: Low spreading after 5 years 3–4" tall and 36" wide.

Achieving an ultimate size in 15 years of 4" tall by 8' spread.

*Overall habit.*—Evergreen conifer, a prostrate shrub, ground hugging habit, maintaining a well foliated crown.

Flowers: apparently insignificant and inconspicuous as is characteristic of the species, not systematically observed; the gender of this plant has not been determined.

Fruit: no berries have been observed on this plant to date; this plant appears to be barren.

Foliage:

*Juvenile.*—Shape: needle-like, acicular. Size: 2–6 mm long; 1–2 mm wide. Arrangement: slightly spreading at a 45 degree angle. Glaucous bloom: present on new foliage. Color: With glaucous bloom: Sung Green 000658/2 compared to Carnation Green 00058 for the parent 'Wiltonii' Outer leaf surface: Spinach Green 0960/3 as compared to Lavender 000761 for the parent 'Wiltonii'

*Mature.*—Shape: scale-like, subulate. Size: 1.5 mm–3 mm long; 1 m–2 mm wide at base. Arrangement: adhering closely to the stems. Glaucous bloom: prominent on new growth. Color: Lavender Green 000761/3 and Spinach Green 0960/3.

*Texture.*—Approximately 99% appears to be soft adult foliage. Approximately 1% appears to be sharp juvenile foliage. Sample used is a 5 year plant.

I claim:

1. A new and distinct selection of *Juniperus horizontalis* plant as substantially shown and described herein, that is characterized particularly as a novelty by the unique combination of a brillant silvery blue color and the ability to retain a dense crown that does not open and become bare with age.

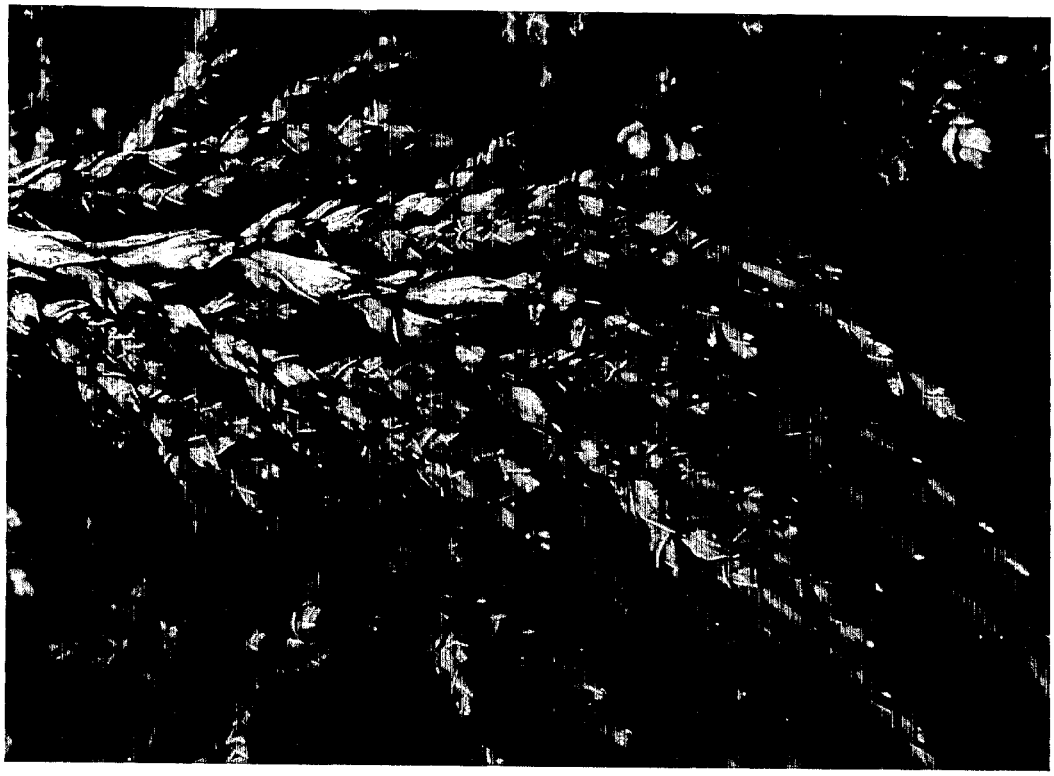
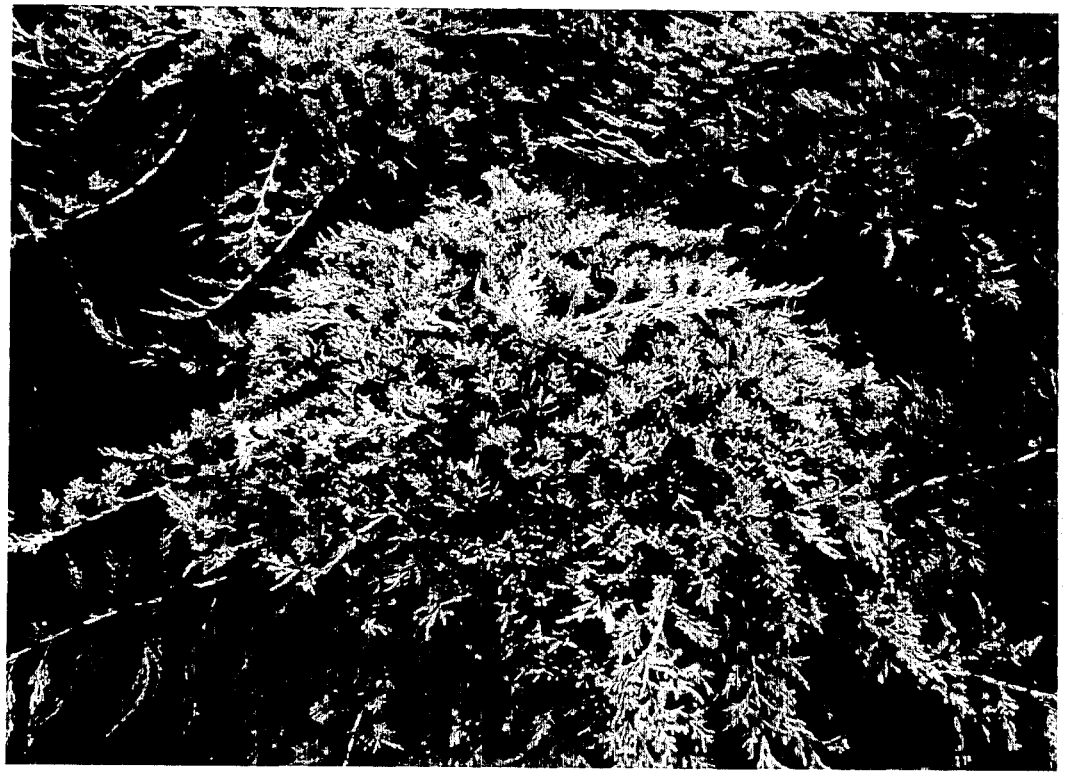

* * * * *